United States Patent [19]

Fogarty et al.

[11] Patent Number: 4,479,497

[45] Date of Patent: Oct. 30, 1984

[54] DOUBLE LUMEN DILATATION CATHETER

[75] Inventors: Thomas J. Fogarty, 770 Welch Rd., Palo Alto, Calif. 94304; Albert K. Chin, San Francisco, Calif.

[73] Assignee: Thomas J. Fogarty, Palo Alto, Calif.

[21] Appl. No.: 440,824

[22] Filed: Nov. 12, 1982

[51] Int. Cl.³ ............................................. A61M 29/02
[52] U.S. Cl. .................................. 128/344; 128/348.1; 604/103
[58] Field of Search .................... 128/344, 325, 348.1; 604/96–103

[56] References Cited

U.S. PATENT DOCUMENTS 3,428,046 2/1969 Remer et al. ........................ 128/344
4,271,839 6/1981 Fogarty et al. ...................... 128/344

FOREIGN PATENT DOCUMENTS 835281 12/1938 France .................................. 128/344

Primary Examiner—Michael H. Thaler
Attorney, Agent, or Firm—Limbach, Limbach & Sutton

[57] ABSTRACT

A dilatation catheter is provided with an elongated balloon element having a distal evertable dilating portion and a connector portion having a radially pleated proximal end. An always-open lumen of the catheter is defined in part by the balloon.

6 Claims, 5 Drawing Figures

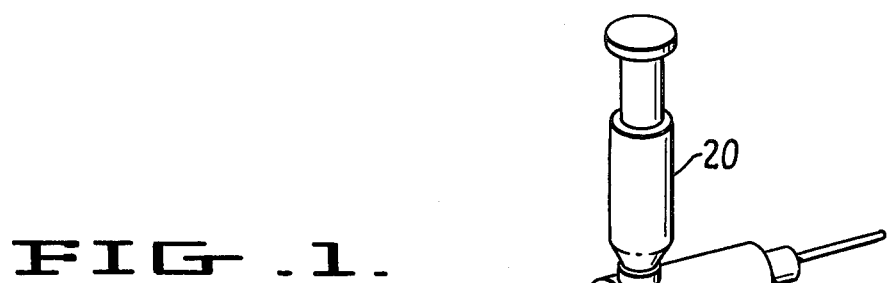
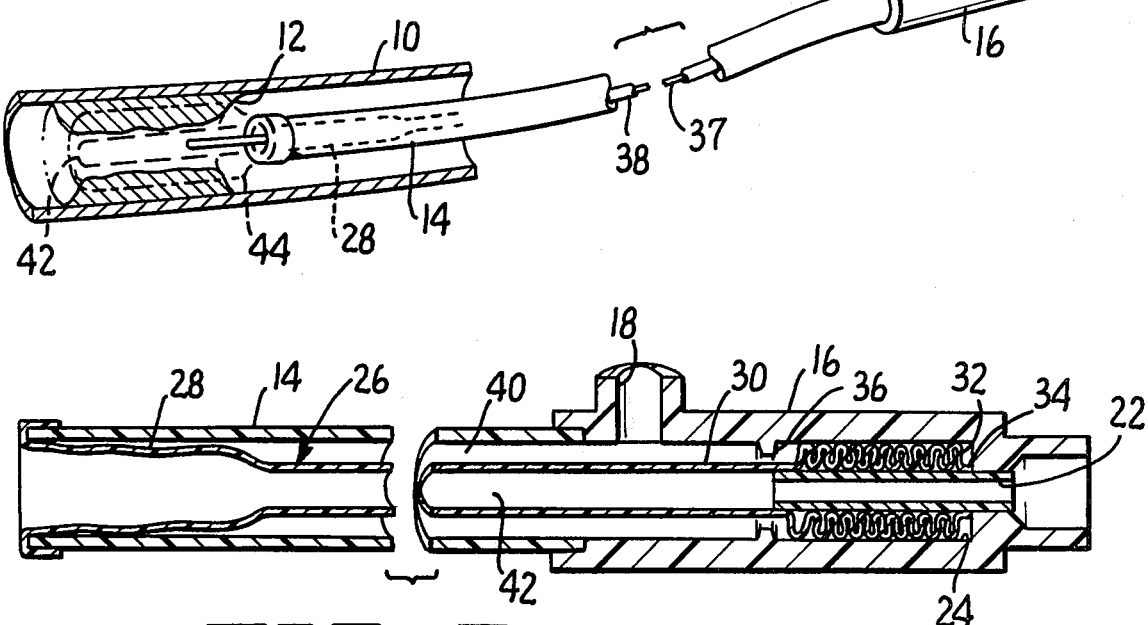
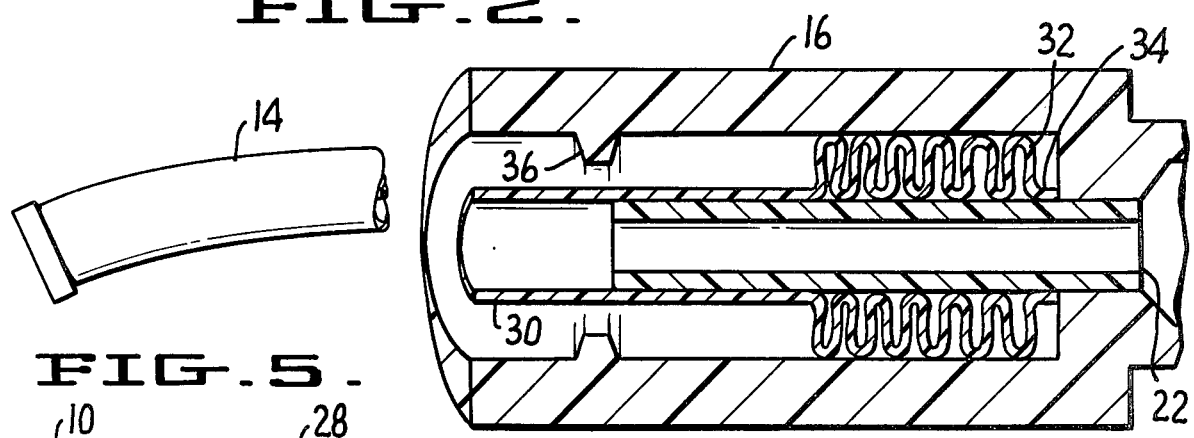
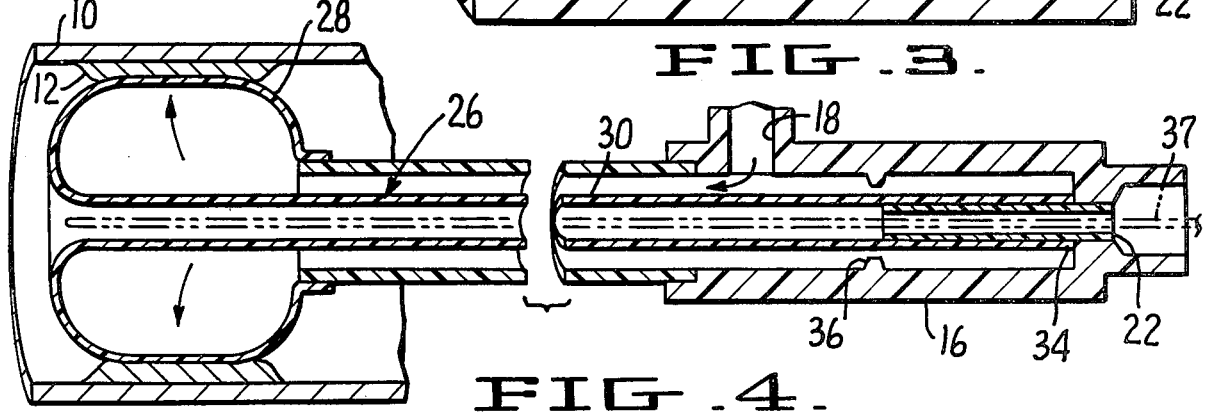

DOUBLE LUMEN DILATATION CATHETER

BACKGROUND OF THE INVENTION

1. Field of the Invention

The invention relates to a dilatation catheter having an evertable balloon element which is attached to the distal end of the catheter and stored in inverted condition in the catheter. The improved catheter of the invention comprises an elongated annular balloon having a distal dilating portion and a proximal, pleated connector portion which interconnects the dilating portion with the interior of the catheter and which enables the provision of a passageway through the catheter which always remains open.

2. Description of the Prior Art

The closest prior art of which we are aware is the third embodiment (FIGS. 7-10) of our prior patent, Fogarty et al. No. 4,271,839.

SUMMARY OF THE INVENTION

The catheter of the invention is provided with an annular balloon of substantial length. The proximal end of this balloon is provided with radial pleats. The distal end of the balloon is attached to the distal end of the catheter and is stored in inverted condition within the catheter. As a pressurized gas or liquid is admitted into the annular space defined between the balloon and the catheter tube, the distal end of the balloon is caused to evert from the catheter to thereby cause a depletion of the pleated condition of the proximal end of the balloon.

DESCRIPTION OF THE DRAWING

FIG. 1 is a view in perspective illustrating an occluded vessel and the catheter of the invention in proximity to the occlusion.

FIG. 2 is an enlarged view in diametral section of the catheter of FIG. 1.

FIG. 3 is a still further enlarged view in diametral section of that portion of the catheter containing the pleated proximal end of the balloon.

FIG. 4 is a view in diametral section of the catheter illustrating the condition of the balloon when it is being used to dilate an occlusion.

FIG. 5 is a view in elevation of a distal end of a catheter according to the invention, showing the distal end of the catheter as being provided with a preformed bend.

DESCRIPTION OF THE PREFERRED EMBODIMENT

FIG. 1 illustrates a blood vessel 10 partially occluded by an occlusion 12.

The catheter comprises a catheter body 14, a catheter housing 16 to which the body 14 is fixedly connected, a balloon inflation port 18, a fluid syringe 20 in feed relation to port 18, an open-ended tube 22 fixedly positioned within the housing 16 and defining with the interior of the latter an annular storage chamber 24, and an annular, elongated balloon 26 having a dilating portion 28 and a connecting portion 30, the latter being provided with a multi-pleated proximal portion 32 which is laid up about the tube 22 within chamber 24. The end 34 of the pleated portion 32 of the balloon is bonded or otherwise fixedly attached to the tube 22 which is in turn fixedly attached to the housing 16. The housing 16 is provided with an annular constriction 36 which serves to retain the pleated portion of the balloon in storage condition about tube 22.

A typical way of installing the catheter at the treatment site, as shown in FIG. 1, is to thread a guide wire 37 through the vessel 10 to the occlusion 12, thread a length of small catheter 38 onto wire 37 for the purpose of serving as a protection for the balloon 26 against wire 37, and to then move the catheter along the wire until the catheter is positioned as shown in FIG. 1. The small catheter 38 and the wire 36 are then withdrawn.

The syringe 20 is then operated to force pressurized fluid into the outer lumen 40 of the catheter. This causes the dilating portion 28 of the balloon to evert from the catheter in anisotropic fashion, as indicated by the dotted outline 42 in FIG. 1. After the dilating portion 28 has been fully everted from the catheter in this manner, a continued supply of the pressurized fluid into a space 40 causes the balloon portion 28 to radially expand, as indicated by dotted outline 44, to compress or dilate occlusion 12. Elongation of the balloon is accompanied by a depletion of the pleated portion 32 of the balloon.

Tube 22 and balloon 26 define an interior, always-open lumen 42 for the catheter.

The balloon 26 is made of a non-elastomeric material, such as polyethylene.

The dilating balloon, or balloon portion 28, and the connecting balloon, or balloon portion 30, may be of the same diameter, that is, together the two balloon portions may constitute a single uniform balloon, or the two balloon portions may be of different diameters, as shown in FIG. 2. A connecting balloon of a smaller diameter than the dilating balloon makes for less friction to occur between the inner walls of the catheter and the surface of the connecting balloon during eversion of the dilatation balloon.

The dilating and connecting balloons may be formed in one piece, as, for example, in one extrusion, or they may both be attached to a short tube or connector, or they may be separate but bonded together.

The provision of the pleated balloon portion 32 serves a plurality of purposes. It allows storage of an appreciable length of connecting balloon on a very small length of supporting tube 22. It allows the pleated or stored part of the connecting balloon to lengthen with little friction to impede the progress of eversion of the dilating balloon. The combination of pleated balloon portion 32 and supporting tube 22 insures the presence in the catheter of an unobstructed inner lumen through which various substances or objects may be passed. The pleated balloon portion constitutes a storage means for the excess length of connecting balloon without the danger of turns or kinks occuring in the connected balloon to close off the inner lumen.

The pleated portion 32 is held in place about tube 22 by the constriction 36 in the housing 16. The constriction allows free movement of the connecting balloon during the eversion-inversion movements of the balloon.

A further feature of the subject catheter is that the catheter body may be provided with a preformed bend as shown in FIG. 5.

Standard angiography catheters incorporate preformed bends in their distal portions to aid in the passage of the catheter into specific arteries, i.e. to follow one branch instead of another at a junction. The subject catheter may be provided with such a preformed bend. This feature, taken with the presence of the always-open central lumen and the consequent capability of the catheter of being passed over a guide wire, allows the subject catheter to be used in a manner similar to methods and techniques customarily used by angiographers. For example, the following sequence may be followed: a guide wire, such as 37, may be passed under fluoroscopic visualization to the area of stenosis; a small plain catheter, such as 38, may be passed from the proximal to the distal end of the subject catheter, thereby allowing the subject catheter to be advanced over the guide wire without difficulty or damage. Once the subject catheter has been positioned proximal to the stenosis, as in FIG. 1, the guide wire and small plain catheter may both be removed, or the guide wire only may be removed, or the guide wire and small plain catheter may both be left in place. In the latter event, the dilating balloon 28 everts over the guide wire to dilate the stenosis.

What is claimed is:

1. A catheter comprising an elongated tubular catheter body, a catheter housing secured to the body, an open-ended tubular member carried by said housing axially therein, annular balloon means extending along said body into said housing, said balloon means comprising a dilatation portion and a connector portion, said dilatation portion being inverted within said body, being evertable therefrom, and having a mouth peripherally sealed to the distal end portion of said body, said connector portion interconnecting said dilatation portion and said housing and having a pleated section sleeved over said tubular member, said balloon means defining with said body and housing a lumen for the inflation and deflation of the dilatation portion of said balloon means, said balloon means with said tubular member defining an open lumen extending centrally through said catheter, and said pleated section being adapted to be depleated relative to said tubular member during elongation of said connector portion upon eversion movement of said dilatation portion.

2. The catheter of claim 1, wherein said pleated section is formed in the proximal end of the connector portion and attached to the tubular member, said pleated section is provided with a plurality of radially directed pleats housed within an annular chamber defined between said tubular member and said housing, said pleats being adapted to be depleated during elongation movement of said connector portion upon eversion movement of said dilatation portion and to be restored during retraction movement of said connector portion during inversion of said dilatation portion.

3. The catheter of claim 2, including constriction means extending radially inwardly of said housing and adapted to maintain said pleats within said annular chamber while leaving said connector portion free for elongation and retraction movement.

4. The catheter of claim 3, said dilatation portion of said balloon means, when inverted within said body, being of a greater diameter than said connector portion.

5. A catheter comprising an elongated tubular catheter body, a catheter housing secured to the body, an open-ended tubular member carried by said housing axially therein, annular balloon means extending along the interior of said body into said housing, said balloon means having the distal end portion thereof peripherally sealed to the distal end portion of said body and having the proximal end portion thereof secured to the interior of said housing through a pleated tubular section of said proximal end portion sleeved over said tubular member, and means to introduce pressurized fluid between said body and balloon means to cause said balloon means to elongate and the distal portion thereof to evert from said body and then to expand, said pleated section being adapted to be depleated relative to said tubular member during elongation of said balloon means and said catheter having a permanently open central lumen defined by said balloon means and the tubular member.

6. The catheter of claim 5, the distal end of said body having a preformed bend.

* * * * *